(12) United States Patent
Notté et al.

(10) Patent No.: US 8,802,883 B2
(45) Date of Patent: Aug. 12, 2014

(54) METHOD FOR THE MANUFACTURE OF DIALKYLPHOSPHITES

(75) Inventors: Patrick Notté, Wavre (BE); Albert Devaux, Mont-Saint-Guibert (BE)

(73) Assignee: Straitmark Holding AG, Zug (CH)

( * ) Notice: Subject to any disclaimer, the term of this patent is extended or adjusted under 35 U.S.C. 154(b) by 0 days.

(21) Appl. No.: 13/322,434

(22) PCT Filed: May 28, 2010

(86) PCT No.: PCT/EP2010/057424
§ 371 (c)(1),
(2), (4) Date: Feb. 17, 2012

(87) PCT Pub. No.: WO2010/136565
PCT Pub. Date: Dec. 2, 2010

(65) Prior Publication Data
US 2012/0190877 A1    Jul. 26, 2012

(30) Foreign Application Priority Data

May 28, 2009  (EP) ..................................... 09161395
May 28, 2010  (WO) ................. PCT/EP2010/057424

(51) Int. Cl.
*C07F 9/141*    (2006.01)
(52) U.S. Cl.
USPC ......................................................... 558/114
(58) Field of Classification Search
USPC .................................... 558/87, 114
See application file for complete search history.

(56) References Cited

U.S. PATENT DOCUMENTS

| | | | |
|---|---|---|---|
| 4,342,709 A | 8/1982 | Jaffe | |
| 5,344,951 A | 9/1994 | Kadkhodayan et al. | |

FOREIGN PATENT DOCUMENTS

| | | |
|---|---|---|
| CN | 101250199 | 4/2012 |
| DE | 128755 | 11/1973 |
| DE | 116457 | 11/1975 |
| DE | 108755 | 12/1976 |
| DE | 222596 | 5/1985 |
| DE | 4121696 | 1/1993 |
| GB | 1299325 | * 12/1972 |
| HU | 196817 | 1/1987 |
| HU | 199149 | 1/1990 |
| HU | 207334 | 3/1993 |
| WO | 2004024742 | 3/2004 |
| WO | 2009068636 | 6/2009 |
| WO | 201005556 | 2/2010 |

OTHER PUBLICATIONS

Roberts et al, Modern Experimental Organic Chemistry, 1979, Saunders College, 3rd ed., p. 542 and 548(4 pages in total including the cover sheets).*

* cited by examiner

*Primary Examiner* — T. Victor Oh
(74) *Attorney, Agent, or Firm* — Samuel Digirolamo; Husch Blackwell LLP

(57) ABSTRACT

A method for the manufacture of dialkyl phosphites is disclosed wherein a P—O component containing from 1 to 6 P—O—P bonds in the molecule is reacted with an alcohol and a carboxylic acid ester having from 1 to 6 carbon atoms in the alkyl group and from 5 to 20 carbon atoms in the esterifying alkyl group of the ester. The dialkyl phosphites are formed under simultaneous removal by distillation of the carboxylic acid formed.

13 Claims, No Drawings

METHOD FOR THE MANUFACTURE OF DIALKYLPHOSPHITES

CROSS REFERENCE TO RELATED APPLICATIONS

This Application is a U.S. National Phase patent application of International Application PCT/EP2010/057424, filed 28 May 2010, which claims the benefit of priority from European Patent Application No. 09161395.0 filed on 28 May 2009. The disclosures of International Application PCT Application No. PCT/EP2010/057424 and European Patent Application No. 09161395.0 are incorporated herein by reference.

This invention concerns a method for the manufacture of dialkyl phosphites starting from P—O component containing from 1 to 6 P—O—P bonds in the molecule comprising the step of reacting the P—O with an alcohol, R'OH, and an ester of a $C_{1-6}$ carboxylic acid, whereby the esterifying alkyl group contains from 5 to 20 carbon atoms, in specifically defined molar ratios of the esterifying alcohol, R'OH and P—O. This mixture is reacted whereby the carboxylic acid formed is distilled off simultaneously. This method yields practically a very good conversion of the P—O reactant to dialkyl phosphite with very low levels of undesirable by-products and high selectivity. In preferred executions, the P—O reactant can be represented by liquid $P_4O_6$.

Dialkyl phosphites have been known for a long time and their importance as intermediates, among others, for synthesizing desirable compounds had been established accordingly. A large variety of approaches had been investigated for the synthesis of dialkyl phosphites. CN 101250199 pertains to a method for preparing diisopropyl phosphite from $PCl_3$ and isopropanol. DE 4121696 describes a process for the preparation of dialkyl phosphites. The treatment of a mixture of methyl- and dimethyl phosphite with acetic anhydride and methanol in benzene resulted in a product containing a high level of dimethyl phosphite. Several publications, HU 207334, HU 199149 and HU 196817, disclose a process for the manufacture of dialkyl phosphites starting from $PCl_3$.

DD 108755 describes the reaction of $P_4O_6$ vapor and methanol vapour to thus yield a mixture of liquid monoester and gaseous diester.

U.S. Pat. No. 4,342,709 describes a process of producing diethyl phosphites by reacting an excess of triethyl phosphite with phosphorous acid. The triethyl reactant is usually added in excess of 7-10% beyond stoichiometric needs. The process starts from a strictly anhydrous phosphorous acid. To avoid negatives attached to the absorption of water, the phosphorous acid is added under inert gas purging. DD 128755 describes a continuous process for preparing dialkyl phosphites starting from phosphorus trichloride and aliphatic alcohols in the presence of an inert solvent. DOS 1 668 031 pertains to the manufacture, in high yields and purity, of dialkyl phosphites starting from primary or secondary linear or branched alcohols, having at least 5 carbon atoms, with phosphorous acid in an excess of at least 45%.

DD 116457 pertains to a continuous process for the manufacture of mono- and di-alkyl phosphites by reacting: a mixture of alcohol and alkyl phosphite or a mixture of mono- and di-alkyl phosphites to which mixture is added technical grade P(III)-oxide containing elementary phosphorus, while purging with technical nitrogen followed by a distillative separation of the mono- and di-alkyl phosphites formed. DD 108755 divulges a process for the continuous preparation of mixtures of mono- and di-alkyl phosphites by reacting $P_4O_6$ with alcohols in the gaseous phase with high yields. DD 222596 concerns a method for preparing pure alkyl- or aryl-diesters of phosphorous acid starting from a mixture of mono- and di-ester phosphites. This mixture is dissolved in an inert organic solvent and the mono-species is precipitated by leading ammonia gas through the mixture.

U.S. Pat. No. 5,344,951 describes a process for preparing di-esters of phosphorous acid whereby a phosphorous acid solution is reacted with an excess of monohydric alcohol to thus yield dihydrocarbyl phosphite. WO 2004/024742 concerns a method for the joint manufacture of diethyl phosphite and ethylchloride whereby one reacts ethanol and phosphorous trichloride in the presence of an additive from the group of tri-ethyl phosphite, diethyl phosphite and/or ethylchloride. In general, the like dialkyl phosphite preparations yield by-products including alkyl chlorides, olefins and ethers due to the presence of alcohol and HCl in the process.

The prior art unequivocally shows that the dialkyl phosphite manufacturing technology while deserving substantial technological and economical improvements has been substantially stagnant for a long time, at least had not offered any viable solution for a meaningful improvement. The art technology is frequently cumbersome, time consuming, uneconomical and not adapted to the actual and foreseeable commercial needs.

It is a major object of this invention to provide a significantly improved process for the manufacture of dialkyl phosphites. It is another object of this invention to provide a method for the manufacture of dialkyl phosphites from reactants broadly other than mixtures of mono and dialkyl phosphites e.g. pure monoalkyl phosphites. Still another aim of this invention is to provide a one-step manufacture of dialkyl phosphites starting from liquid $P_4O_6$. Still another object herein envisages a method for the manufacture of dialkyl phosphites of improved purity and selectivity commensurate with prevailing needs. Yet another objective herein aims at providing dialkyl phosphites at economically favorable conditions. Still another object of the invention herein contemplates the manufacture of substantially pure/chlorine free dialkyl phosphites.

The term "percent" or "%" as used throughout this application stands, unless defined differently, for "percent by weight" or "% by weight". The term "ppm" stands for "parts per million". The terms "$P_2O_3$" and "$P_4O_6$" can be used interchangeably. The term "liquid $P_4O_6$" embraces neat $P_4O_6$ in the liquid state, solid $P_4O_6$ and gaseous $P_4O_6$, preferably liquid $P_4O_6$. The term "ambient" with respect to temperature and pressure generally means usually prevailing terrestrial conditions at sea level e.g. temperature is about 18° C. to 25° C. and pressure stands for 990-1050 mm Hg.

The foregoing and other objectives can now be met by means of a method of manufacture whereby P—O—P bonds containing compounds are converted into the corresponding dialkyl phosphites. In more detail, this invention pertains to a method for the manufacture of dialkyl phosphites starting from P—O component containing from 1 to 6 P—O—P bonds in the molecule comprising the step of:

a) reacting a mixture of the P—O component and R'OH, expressed in molar ratios of R'OH:P—O of at least 1:1 to 6:1 wherein R' is selected from alkyl groups having from 5 to 20 carbon atoms in branched or linear configuration; and an acid ester having the formula:

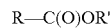

wherein R' has the meaning stated above, and wherein R represents an alkyl chain having from 1 to 6 carbon atoms, whereby the minimum number of mole(s) of R—C(O)OR', per P atom in the P—O molecule, required for the method (and the stoichiometric conversion of one mole of said P—O to dialkyl phosphite), "z", is determined by $z=2n-m$, wherein m is the number of P—O—P bonds in the P—O molecule and n is the number of P atoms in that molecule, by adding the P—O to the R'OH, simultaneously with or separately from the acid ester; at a temperature in the range of from 40° C. to 180° C., preferably from 70° C. to 150° C., particularly from 90° C. to 130° C., for a period of from 10 minutes to 10 hours, preferably of 15 minutes to 6 hours; under simultaneous removal by distillation of the carboxylic acid formed.

In a preferred execution of this invention, the dialkylphosphite component is prepared by adding $P_4O_6$ to the reaction medium containing R'OH simultaneously with or separately from the acid ester. The reaction medium is generally the alcohol itself although a suitable solvent, which is inert in relation to P—O, R'OH and the acid ester, can optionally be used. Suitable solvents are preferably as follows: anisole; fluorobenzene; chlorinated hydrocarbons such as chlorobenzene, tetrachloroethane, tetrachloroethylene; polar solvents like sulfolane, diglyme, glyme, diphenyl oxide, polyalkylene glycol derivatives with capped OH groups such as OR where R is a low alkyl group; aliphatic hydrocarbons such as hexane, heptane, cyclohexane; non-cyclic ethers like dibutyl ether, diisopropyl ether, and dipentyl ether; cyclic ethers like tetrahydrofuran and dioxane; aromatic hydrocarbons like toluene, xylene; organic nitriles like acetonitrile; silicon fluids like polymethylphenyl siloxane or mixtures thereof. Most preferred are solvents distilling as azeotropes with the carboxylic acid to be removed from the system e.g. toluene to remove acetic acid.

The $P_4O_6$ can be represented by a substantially pure compound containing at least 85%, preferably more than 90%; more preferably at least 95% and in one particular execution at least 97% of the $P_4O_6$. While tetraphosphorus hexa oxide, suitable for use within the context of this invention, can be manufactured by any known technology, in preferred executions the hexa oxide can be prepared in accordance with the method of WO 2009/068636 and/or PCT/EP2009/064988, entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 to 2000 K, by removing the heat created by the exothermic reaction of phosphorus and oxygen, while maintaining a preferred residence time of from 0.5 to 60 seconds followed by quenching the reaction product at a temperature below 700 K and refining the crude reaction product by distillation. The hexa oxide so prepared is a pure product containing usually at least 97% of the oxide. The $P_4O_6$ so produced is generally represented by a liquid material of high purity containing in particular low levels of elementary phosphorus, $P_4$, preferably below 1000 ppm, expressed in relation to the $P_4O_6$ being 100%. The preferred residence time is from 5 to 30 seconds, more preferably from 8 to 30 seconds. The reaction product can, in one preferred execution, be quenched to a temperature below 350 K.

The term "liquid $P_4O_6$" embraces, as spelled out, any state of the $P_4O_6$. However, it is presumed that the $P_4O_6$ participating in a reaction at a temperature of from 40° C. to 180° C. is necessarily liquid or gaseous although solid species can, academically speaking, be used in the preparation of the reaction medium.

The P—O component can be represented by $P_4O_6$, or partially hydrated species thereof, containing from 1 to 6 P—O—P bonds in the molecule. Examples of suitable species of the P—O component include: pyrophosphorous acid, $H_4P_2O_5$, containing one P—O—P bond; $P_4O_6$ containing six P—O—P bonds; and partially hydrated species thereof containing 2, 3, 4 and 5 P—O—P bonds respectively. Partially hydrated $P_4O_6$ can lead to hydrolysis products containing 2, 3, 4 or 5 P—O—P bonds. For reasons of convenience and operational expertise, the P—O component is preferably represented by $P_4O_6$ of high purity containing very low levels of impurities, in particular elemental phosphorus, $P_4$, at a level below 1000 ppm, usually below 500 ppm and preferably not more than 200 ppm, expressed in relation to the $P_4O_6$ being 100%. The P—O component can be represented by uniform ingredients having e.g. a uniform number of P—O—P bonds or by mixtures having a distribution of P—O—P bonds as may occur in partially hydrated species of $P_4O_6$. Obviously, in such case the number of P—O—P stands for an average number of P—O—P bonds. Suitable P—O components can also be prepared starting from $PCl_3$ by partial hydrolysis, or by reacting $PCl_3$ and phosphorous acid or by reacting $P_4O_6$ and phosphorous acid or by partial hydrolysis of $P_4O_6$. The P—O component can be represented by mixtures/combinations of different reagents e.g. $PCl_3$, phosphorous acid and water subject to the presence of at least one P—O—P bond in the molecule. The level of water to be employed is limited (in molar terms) to 4 $H_2O$ per $P_4O_6$. If the P—O is represented by a component having less than 6 P—O—P bonds, then the water level is reduced proportionally so that at least one P—O—P bond is present in the P—O component for use in the method herein. In the event a chlorine containing starting materials, e.g. $PCl_3$ and combinations thereof, are used the level of chlorine shall be kept below 1000 ppm, usually below 500 ppm, preferably below 200 ppm, expressed in relation to the P—O material being 100%.

The acid ester having the formula R—C(O)OR' is a well known class of materials a fair number of species of which are commercially available or can be made available routinely in accordance with needs. The carboxylic acid group R contains from 1 to 6 carbon atoms, preferably from 1 to 4 carbon atoms, in linear or branched configuration. The group R' in the alcohol R'OH and in the acid ester R—C(O)OR' is represented by an alkyl group having from 5 to 20 carbon atoms, preferably from 5 to 12 carbon atoms, in particular from 5 to 8 carbon atoms, in branched or linear configuration. While R' in the alcohol and in the acid ester can be selected independently, in preferred embodiments, identical R's are used in both the alcohol and the acid ester.

The minimum number of mole(s) of R—C(O)OR', per P atom in the P—O molecule, required for the complete conversion of one mole of the P—O to dialkyl phosphite, and, thus, for the inventive process, z, is determined by $z=2n-m$, wherein m is the number of P—O—P bonds in the P—O molecule and n is the number of P atoms in that molecule.

The R'OH is represented by alcohols having an alkyl group of from $C_5$ to $C_{20}$, in linear or branched structure, preferably an alkyl group having from 5 to 12 carbon atoms, in particular from 5 to 8 carbon atoms. The R'OH is used in relation to P—O in molar ratios of from R'OH:P—O of at least 1:1 to 6:1. The ratios R'OH:P—O of 1:1 to 6:1 are related to the number of P—O—P bonds in the P—O component. The term "at least" means that the level of R'OH can be increased to e.g. 8:1 without adversely affecting the system. Any excess of R'OH can routinely be recycled into the system and thus doesn't affect the economics of the inventive method.

The reaction in accordance with this invention is conducted in a manner routinely known in the domain of the technology. As illustrated in the experimental showings, the method can be conducted by combining the essential reaction partners and heating the reaction mixture to a temperature usually within the range of from 45° C. to 180° C., more preferably 70° to 150° C., in particular 90 to 130° C. The upper temperature aims at preventing any substantial undue decomposition of the reactants or of the intermediates formed in these reactions. It is understood and well known that the decomposition temperature of the reaction partners can vary depending upon physical parameters, such as pressure and the qualitative and quantitative parameters of the ingredients in the reaction mixture.

The inventive reaction can be conducted at ambient or reduced pressure and, depending upon reaction temperature, under distillation thereby eliminating potential excess alcohol and the carboxylic acid formed, possibly as an azeotrope with a solvent. The duration of the reaction can vary from virtually instantaneous, e.g. 10 minutes, to an extended period of e.g. 10 hours. In one method set up, the P—O, the alcohol and the ester are added to the reactor followed by heating this mixture gradually to a temperature of from 70° to 150° C. This reaction can be carried out under ambient, or reduced, pressure with distillation.

In yet another operational sequence, the reaction can be conducted in a combined distillation and pressure arrangement. Specifically, the reaction vessel containing the reactant mixture is kept under ambient, or reduced, pressure at the selected reaction temperature. The mixture is then, possibly continuously circulated through a reactor operated under autogeneous (autoclave principle) pressure build up thereby gradually adding the additional reaction partners in accordance with needs. The reaction is substantially completed under pressure and the reaction mixture then leaves the closed vessel and is recycled to the reactor where distillation of the excess alcohol and carboxylic acid formed will occur.

The reaction can thus be conducted as a batch process by heating the initial reactants under autogeneous, possibly under reduced pressure at 70° C. to 150° C.

In yet another arrangement, the method can be represented by a semi-continuous set-up whereby the reaction is conducted continuously whereas preliminary reactions between e.g. the P—O and the alcohol can be conducted batch-wise.

The dialkyl phosphite reaction products can, if needed, be recovered from the reaction product by conventional means including, in particular, vacuum distillation.

The dialkyl phosphites can be used as intermediates, e.g., for beneficially synthesizing compounds which were known to be difficult to make. As an example, 2-phosphonobutyl-1, 2,4-tricarboxylic acid can be made starting from dialkylphosphites as follows:
1: reacting dimethyl phosphite with methylmaleate; followed by
2: reacting the system resulting from 1: with methyl acrylate in the presence of sodium methoxide; followed by
3: hydrolysing the ester groups formed under 2: with water in the presence of hydrochloric acid.

Accordingly, in one aspect of the invention there is provided a method for preparing 2-phosphonobutyl-1,2,4-tricarboxylic acid by preparing dimethylphosphite according to the inventive method and further conversion to 2-phosphonobutyl-1,2,4-tricarboxylic acid as described above.

The invention is further illustrated by the following examples without limiting it thereby.

EXAMPLES

Example 1

22 g (0.1 mole) of $P_4O_6$ heated at 40° C. were added dropwise over 25 minutes to 106 g (1.2 moles) of 1-pentanol under stirring. While the reaction mixture was maintained at 40° C., 52.56 g (0.4 mole) of 1-pentyl acetate were added. 60 ml of dried toluene were added to the reaction mixture and heating under stirring was applied in order to reach 122 to 135° C. to distil toluene rich liquid. This distillation process was maintained over 2 hours 50 minutes with 2 other additions of 60 ml of dried toluene.

$^{31}P$ NMR analysis of the crude reaction mixture showed the presence of 0.5% w/w (1.2 mole %) of $H_3PO_3$, 19.6% w/w (26.1 mole %) of mono 1-pentyl phosphite and 79.8% w/w (72.6 mole %) of di 1-pentyl phosphite.

Example 2

22 g (0.1 mole) of $P_4O_6$ heated at 40° C. were added dropwise over 25 minutes to 106 g (1.2 moles) of 1-pentanol under stirring. While the reaction mixture was maintained at 40 to 50° C., 52.56 g (0.4 mole) of 1-pentyl acetate and 10 ml of 1-pentanol were added. Then, a fraction of 60 ml of dried toluene were added to the reaction mixture and heating under stirring was applied to reach a temperature in the range of 120 to 135° C. with distillation of toluene rich liquid. After 45 minutes of distillation, 60 ml of dried toluene and 60 ml of 1-pentyl acetate were added to the reaction mixture and the heating/distillation process were further continued. This distillation process was then maintained over 4 hours 30 minutes with 4 other additions of 60 ml fractions of dried toluene.

$^{31}P$ NMR analysis of the crude reaction in $CDCl_3$ showed the presence of 0.6% w/w (1.5 mole %) of $H_3PO_3$, 19.6% w/w (26.0 mole %) of mono 1-pentyl phosphite and 79.6% w/w (72.4 mole %) of di 1-pentyl phosphite.

The invention claimed is:

1. A method for the manufacture of di-alkylphosphites starting from a P—O component containing from 1 to 6 P—O—P bonds in the molecule comprising the step of:
   a) reacting a mixture of R'OH and P—O, expressed in molar ratios of R'OH:P—O of at least 1:1 to 6:1,
   wherein R' is selected from alkyl groups having from 5 to 20 carbon atoms in branched or linear configuration; and an acid ester having the formula:

wherein R' has the meaning as stated above, wherein R represents an alkyl chain having from 1 to 6 carbon atoms, wherein the minimum number of mole(s) of R—C(O)OR' per P atom in the P—O molecule, required for the method is represented by z and z is determined by the formula z=2n−m, wherein m is the number of P—O—P bonds in the P—O molecule, and n is the number of P atoms in the P—O molecule; by adding the P—O component to the R'OH, simultaneously with or separately from the acid ester; at a temperature in the range of from 40° C. to 180° C. for a period of from 10 minutes to 10 hours under simultaneous distillation of the carboxylic acid formed.

2. The method in accordance with claim 1, wherein R in the carboxylic acid has from 1 to 4 carbon atoms.

3. The method in accordance with claim 1, wherein the P—O component is represented by $P_4O_6$.

4. The method in accordance with claim 3, wherein the $P_4O_6$ is liquid.

5. The method in accordance with claim 1, wherein the P—O component is added to the reaction medium containing the R'OH and the acid ester.

6. The method in accordance with claim 1, wherein the P—O has less than 1000 ppm of elemental phosphorus, $P_4$, expressed in relation to the P—O component being 100%.

7. The method in accordance with claim 1, wherein the alkyl groups in the alcohol, R'OH, and acid ester are identical.

8. The method in accordance with claim 1, wherein the molar ratio of R'OH:P—O is in the range of from 1:1 to 8:1.

9. The method in accordance with claim 1, wherein the P—O component is added to the reaction medium containing water in a molar level of 4 or less $H_2O$ per P—O.

10. The method in accordance with claim 1, wherein the alkyl groups, R', in the alcohol and the acid ester have from 5 to 12 carbon atoms.

11. The method in accordance with claim 1, wherein the alkyl group, R', in the alcohol has from 5 to 8 carbon atoms.

12. The method in accordance with claim 1, wherein the reaction is conducted for a period of 15 minutes to 6 hours at a temperature from 70° C. to 150° C.

13. The method in accordance with claim 1, wherein the P—O component is prepared starting from $PCl_3$, having less than 400 ppm of chlorine, expressed in relation to the P—O component (100%).

* * * * *